(12) United States Patent
Matsumoto (10) Patent No.: US 6,783,987 B2
(45) Date of Patent: Aug. 31, 2004

(54) METHOD FOR OBTAINING COMPONENTS FROM CULTURED LEUCOCYTE

(76) Inventor: Tsukasa Matsumoto, Higashi-Tamagawa 1-23-11, Setagaya-ku, Tokyo (JP)

( * ) Notice: Subject to any disclaimer, the term of this patent is extended or adjusted under 35 U.S.C. 154(b) by 0 days.

(21) Appl. No.: 10/045,028

(22) Filed: Jan. 15, 2002

(65) Prior Publication Data

US 2002/0155613 A1 Oct. 24, 2002

Related U.S. Application Data

(63) Continuation-in-part of application No. 09/520,624, filed on Mar. 7, 2000, now abandoned.

(30) Foreign Application Priority Data

Dec. 9, 1999 (JP) .......................................... 11-350518

(51) Int. Cl.⁷ .............................................. G01N 33/48
(52) U.S. Cl. ......................... 436/63; 436/174; 436/177; 435/2; 435/29; 424/529; 424/534
(58) Field of Search ............................. 436/48, 10, 17, 436/63, 174, 175, 177; 435/2, 29, 30; 424/529, 534

(56) References Cited

U.S. PATENT DOCUMENTS

| | | | |
|---|---|---|---|
| 4,004,975 A | | 1/1977 | Lionetti et al. |
| 4,465,669 A | * | 8/1984 | Wissler et al. ................ 514/21 |
| 4,468,379 A | | 8/1984 | Gottlieb |
| 5,427,664 A | | 6/1995 | Stoev et al. |
| 5,776,672 A | | 7/1998 | Hashimoto et al. |
| 6,177,106 B1 | | 1/2001 | Matsumoto ................ 424/533 |

* cited by examiner

*Primary Examiner*—Maureen M. Wallenhorst
(74) *Attorney, Agent, or Firm*—Hall, Myers, Vande Sande & Pequignot (57) ABSTRACT

A method for obtaining leucocyte components from human blood including (A) a first step for fracturing the cell membrane of leucocytes of human blood by using a freezing and defrosting method, a supersonic application, laser irradiation, an osmotic pressure changing method, a vacuum chamber, or the like and (B) a second step for separating and collecting the leucocyte-components containing the leucocytes with fractured cell membranes from the blood liquid resulted from the first step by way of a centrifugal precipitation technique or an electrophoresis technique. After being separated and collected, the leucocyte components are, respectively, subjected to various therapeutic tests using blood samples collected from patients suffering from various diseases to determine the therapeutic effects.

8 Claims, 11 Drawing Sheets

Classification of cells of incubated leucocytes Part I

FIG. 1a Amaebaid type

FIG. 1b Balloon type

FIG. 1c Un-changed type

FIG. 1d Carnival type

FIG. 1e Caterpillar type

FIG. 1f Caterpillar type

FIG. 1g Caterpillar type

FIG. 2a  TLRC+pseud 0 time

FIG. 2b  TLRC+pseud 24h

FIG. 2c  MLRC+pseud 0 time

FIG. 2d  MLRC+pseud 24h

FIG. 2e  BLRC+pseud 0 time

FIG. 2f  BLRC+pseud 24h

Incubated leucytes (il) and pseudomonas sp.

FIG. 3a
TLRC + pseud sp + il
0 time

FIG. 3b
TLRC + pseud sp + il
39h

FIG. 3c
MLRC + pseud sp + il
0 time

FIG. 3d
MLRC + pseud sp + il
39h

FIG. 3e
BLRC + pseud sp + il
0 time

FIG. 3f
BLRC + pseud sp + il
39h

FIG. 3g

TLRC + pseud + Ab
0 time

FIG. 3h

TLRC + pseud + Ab
26~28h

FIG. 3i

MLRC + pseud + Ab
0 time

FIG. 3j

MLRC + pseud + Ab
26~28h

FIG. 3k

BLRC + pseud + Ab
0 time

FIG. 3l

BLRC + pseud + Ab
26~28h

0 Time

BLRC only

FIG. 4a 9 days inc.

Black shells and
Black sesames

FIG. 4b

BLRC + healthy
person's WC

FIG. 4c

Living BLRC

FIG. 4d

Newly discovered function of leucocyte 20 days incubation of fat tissue

Fat tissue only

FIG. 6a

Fat tissue +
FWC(Frozen white blood cell)

FIG. 6b 20 days incubation of muscle tissue

Muscle tissue only

FIG. 6c

Muscle tissue +
FWC(Frozen white blood cell)

FIG. 6d

Dialysis
ULRBC and LLRBC (♀,52y) in incubator

<4 days after>

—ULRBC— control
FIG. 7a

—LLRBC— control
FIG. 7b

+ healthy person's FWBC
FIG. 7c

+ healthy person's FWBC
FIG. 7d

+ patient's LWBC
FIG. 7e

+ patient's LWBC
FIG. 7f

C-hepatitis
ULRBC and LLRBC (♂,60y) in incubator

<5 days after>
−ULRBC−

+ healthy person's FWBC

FIG. 8a

+ patient's FWBC

FIG. 8b

+ healthy person's LWBC

FIG. 8c

+ patient's LWBC

FIG. 8d

Interaction between leucocyte and erythrocyte
C-Hepatitis   5 days inc.   WN 60 ♂

TLRC

\+ healthy person's FWC
FIG. 9a

\+ patient's FWC
FIG. 9b

\+ healthy person's LWC
FIG. 9c

\+ patient's LWC
FIG. 9d

BLRC

\+ healthy person's FWC
FIG. 9e

\+ patient's FWC
FIG. 9f

\+ healthy person's LWC
FIG. 9g

\+ patients LWC
FIG. 9h

Interaction between the leucocyte and erythrocyte
Auto-immunic hepatitis   T.S 83 ♀   5 days inc.

TLRC control

FIG. 10a

+ healthy person's FWC
Megalo WC+

FIG. 10b

+ healthy person's LWC
Megalo WC−
Black spot+

FIG. 10c

+ patient's LWC
Megalo WC++
Black spot++

FIG. 10d

BLRC control

FIG. 10e

+ healthy person's FWC
Black spot−

FIG. 10 f

+ healthy person's LWC
Black spot−

FIG. 10g

+ patient's LWC
Black spot+

FIG. 10h

METHOD FOR OBTAINING COMPONENTS FROM CULTURED LEUCOCYTE

RELATED APPLICATIONS

This application is a Continuation-in-Part of U.S. patent application Ser. No. 09/520,624, entitled METHOD FOR OBTAINING COMPONENTS FROM CULTURED LEUCOCYTE, filed Mar. 7, 2000, and invented by Tsukasa Matsumoto, now abandoned.

BACKGROUND OF THE INVENTION

1. Field of the Invention

The present invention relates to a method for obtaining components by fracturing the cell membrane of leucocytes in human blood, and separating and collecting the leucocyte components, individually.

2. Prior Art

Conventionally, it has been commonly known that erythrocytes of human blood mainly act as carriers for carrying a large amount of oxygen and carbon dioxide at a high speed, and leucocytes act as phagocytes against various bacteria. However, in practical scenes, erythrocytes also crowd at the inflamed part where a great deal of bacteria exist. It seems that thus crowded erythrocytes act as any biological function in the inflamed part. In addition to this phenomenon, the biological correlation between erythrocytes and leucocytes in such inflamed and bacterial affected parts has not been clearly known. The inventor of the present application previously submitted the patent application titled "Method for fractionating red blood cells" Japanese Patent Application No. Tokugan-Hei 8-215552/1996, corresponding to European Patent Application No. 97102952.5 titled "Method for fractionating red blood cells and antibacterial materials or bacterial proliferation inhibitors produced thereby". The inventor observed the biological function between the erythrocytes and bacteria included in respective three layers fractionated in accordance with the previously applied method.

In detail, the three erythrocyte-samples from the fractionated three layers; i.e., top, middle, and bottom layers, were respectively added into liquid culture medium, and then bacteria sample was inoculated into all of the culture medium to observe the function of live erythrocytes against the inoculated bacteria. In the top layer the bacteria were surrounded with the erythrocytes and thus their bacterial proliferation were inhibited. Although the top layer included leucocytes, these leucocytes did not provide any phagocytosis to the bacteria. The erythrocytes included in the middle layer did not show any aggressive motions towards the bacteria, but the bacterial proliferation were inhibited. The middle layer also included a small amount of leucocytes, which did not show any motions towards the bacteria. The erythrocytes included in the bottom layer did not show any aggressive motions towards the bacteria. Thus, the bacterial proliferation were observed. The bottom layer did not include leucocytes at all.

Since the number of leucocytes in human blood are remarkably increased when bacterial inflammation causes or the size of specific leucocyte is extremely enlarged in bacterial inflamed part, it has been conventionally realized that these phenomena are resulted from the phagocytosis of leucocytes. However, as disclosed in the previously applied invention "Method for fractionating red blood cells" the observation on the action and change of live erythrocytes and leucocytes around bacteria proves that conventional knowledge; i.e., leucocytes only attack bacteria, is not correct.

According to conventional knowledge, erythrocytes comprise single type blood cells having a uniform figure and the same characteristics, while leucocytes comprise several different real cells having nucleus and cytoplasm. Conventionally, leucocytes are classified depending on appearance and staining property into five groups, neutrophil leucocyte, eosinophile leucocyte, basophilic leucocyte, lymphoid cell, and monocyte as disclosed in "Seikagaku Jiten (Encyclopedia of Biochemistry)" published by Tokyo Kagakudoj in. Conventional method for laboratory tests of erythrocytes and leucocytes have been performed as following steps. One drop of blood is placed on a glass plate and is spread into a thin layer using the end of another glass plate. After drying, this blood sample is stained with various staining agents and then the stained sample is observed through an optical microscope. This conventional method, however, leads to following three defects.

(1) As the blood sample is dried, the cells are mummified. Therefore this conventional method is too primitive and coarse to observe such delicate, soft, and volatile cells as the erythrocytes and leucocytes.

(2) In the staining technique, the blood cells and components difficult of staining cannot be observed at all. The part that does not stain easily is ignored and the part that stains easily is over-stained darkly. Accordingly, minute changes cannot be observed.

(3) In biological researches, a phenomenon should be observed from the beginning to the end covering as long a period as possible. The biological truth cannot be known unless the state changing with time is grasped.

Conventionally, Ficoll-Conray method has been known to separate and collect lymphoid cells from leucocytes. Thus collected lymphoid cells have been used in various manners to study the immune system about the leucocytes in human blood. For example, the inventor of the present application found out that remarkable effects were not resulted when the lymphoid cells obtained from a healthy person were administered to the rheumatics, but remarkable effects were resulted when cultured leucocytes of a healthy person were administered to the same patient. Further, the inventor has continuously researched on clinical cases of many rheumatics administered with the cultured leucocytes, and confirmed the superior effects in medical treatment for the rheumatics. The inventor reported and published such therapeutic effects at many academic meetings and in bulletins; as an example, International Rheumatism Conference 1981 held in Paris.

It has been assumed that stale cells are broken into water-soluble fine pieces and transported by flowing blood towards liver and kidney. Although the liver and kidney act as the final wastes treatment, the processes of decomposition and water-solubilization of stale cells prior to the final wastes treatment are not clarified. The inventor used the bottom layer (excluding leucocytes) of the fractionated three layers provided by "Method for fractionating red blood cells" to observe the wastes treatment function of leucocytes. In detail, the bottom layer was added with frozen leucocytes or live leucocytes of the same blood type, and then cultured. As a result, this cultured bottom layer showed that the blood cells of the bottom layer were changed to minute and water-soluble particles rather than the non-treated sample free from leucocytes. Additionally, this effect appeared remarkably in the case of using the frozen leucocytes rather than the live leucocytes. This phenomenon means following two functions. First, leucocytes have the function for treating stale or perished erythrocytes as wastes. The second function is anticipated from the phenomenon of the frozen leucocytes having superior effect to live leucocytes. Some components spread out of the leucocyte-cells fractured during freezing step may act as agents which accelerate the decomposition and water-solubilization of stale or perished erythrocytes.

As discussed above, many clinical tests proved that the cultured leucocytes obtained from a healthy person had effect on specific diseases such as rheumatic disease. However, in actual therapeutic scenes, the cultured leucocytes should be subjected to various tests, for example, the blood check for AIDS virus, prior to administration, and further, should be prepared and stored in a specially controlled space such as an aseptic culture room with meticulous care. Thus therapeutic cost will become high. As an example in an actually performed test-therapy, an administration of cultured leucocytes is performed per four weeks; one course includes six times of administrations; and at least four courses are desired. One administration needs about Yen 50,000 (US$ 550), and thus totally four courses need about Yen 1,200,000 (US$ 13,200). This cost is extremely high for ordinary patients, and therefore on the present stage, actual therapies use steroid drugs which produce harmful aftereffects and anti-inflammatory or analgesic agents which produce temporary pain-free effect.

According to the above observations, the inventor concludes that the correlation between the leucocyte components and the erythrocytes, the therapeutic function of the leucocyte components for various bacteria, and the function of the leucocyte components for treating stale or perished cells should be clarified in order to produce a new drug which is free from harmful aftereffects produced by antibiotics and steroid drugs. Further such leucocytes induced drugs are expected to be applied to the therapy for various cancers, hepatic disease, and renal disease at a low cost. If hepatic disease and renal disease are healed or improved by such new drugs, it is expected to decrease lever and kidney transplant operations which are risky, complicated and high cost operations.

SUMMARY OF THE INVENTION

It is therefore a primary object of the present invention to provide a method for fracturing the cell membrane of leucocytes in human blood to separate and collect leucocyte components.

Another object of the present invention is to provide a method to separate and collect the leucocyte components under the near-live condition.

In order to accomplish the above objects, the present invention provides a method comprising (A) a first step for fracturing the cell membrane of leucocytes in human blood by physical means, and (B) a second step for separating and collecting the leucocyte components from the blood liquid resulted from the first step, containing the leucocytes with fractured cell membranes, by means of a centrifugal precipitation technique or an electrophoresis technique.

Thus separated and collected leucocyte components may be respectively subjected to various therapeutic tests using blood samples collected from patients suffering from various diseases to know the therapeutic effects. One typical example of these therapeutic tests is performed in the following steps.

(1) 5 to 10 ml of blood sample is taken from a patient suffering from cancer, hepatic disease, or renal disease and then separated into three layers; top layer, middle layer, and bottom layer, in the same manner as shown in the method for fractionating red blood cells, disclosed in the prior invention. These three layers are cultured respectively, and their changes are observed through a phase-contrast microscope for a predetermined period. These observed data are recorded by a still camera, video camera, or the like, and used as reference for judging the therapeutic effects.

(2) The three layers are also obtained from the same patient's blood in the same fractionating method, and then added with one group of the leucocyte components separated from a healthy person's blood. The three layers are cultured and the changes of erythrocytes are observed through the same phase-contrast microscope at a predetermined time interval. According to the above works (1) and (2), it is possible to judge which leucocyte component has the therapeutic effect on which kind of diseases.

The physical means used in the first step (A) for fracturing the cell membranes of leucocytes may be selected from (a) a supersonic method for applying the supersonic of 1 MHz to 50 MHz to the blood liquid containing leucocytes to fracture the cell membranes of leucocytes by the vibration caused by the supersonic; (b) a laser method for irradiating the laser of 10 to 100 mW, 50/cm$^2$ for several seconds to several minutes (about 3 minutes) to the same point in the blood liquid containing leucocytes to fracture the cell membranes; (c) an osmotic pressure method for changing the osmotic pressure of the blood liquid containing leucocytes to fracture the cell membranes; (d) a freezing and defrosting method for freezing the blood liquid containing leucocytes at the temperature range from −5 degrees to the absolute zero point and then defrosting this frozen liquid at a room temperature (about 20 degrees) to fracture the cell membranes; and (e) a vacuum method for rapid-reducing the pressure in a vacuum chamber to fracture the cell membranes of the blood liquid containing leucocytes set in the chamber.

The second step (B) for separating and collecting the leucocyte component includes a centrifugal precipitation technique which stirs the blood liquid containing the leucocytes with cell membranes fractured by the first step (A), and then separates the stirred liquid into multiple layers corresponding the leucocyte components by the centrifugal precipitation work. Alternatively, the second step (B) includes an electrophoresis technique which separates the blood liquid containing the leucocytes with fractured cell membranes by the first step (A) into multiple parts corresponding the leucocyte components by the electrophoresis work. Finally, the separated layers or parts are collected separately.

The first step (A) may use the cultured leucocytes obtained from the specific persons who are judged healthy through predetermined health checks.

These and other objects and many of the attendant advantages of the present invention will be readily appreciated as the same becomes better understood by reference to the following detailed description when considered in connection with the accompanying drawings.

BRIEF DESCRIPTION OF THE DRAWINGS

PIGS. 5a, 5b, 5c, 5d, 5e, 5f, 5g, and 5h illustrate photographic data captured through a phase-contrast microscope illustrating the effects of separately incubating both frozen and living white blood cells with lower layer red blood cells.

DETAILED DESCRIPTION OF THE PREFERRED EMBODIMENT

According to one preferred embodiment of the present invention, leucocytes obtained from a healthy person are cultured, and then leucocyte components are separated and collected. Thus collected leucocyte components are added to various blood samples obtained from various patients suffering from diseases in order to find and judge therapeutic effects. Detailed process of the preferred embodiment will be disclosed as follows.

First, leucocytes are separated from human blood containing all blood ingredients in a typical conventional manner. 200 ml of human blood obtained from a healthy person (who was passed through all possible health checks and blood checks at present stage) is added into 300 ml of Dextran-70 (commercially available by Tokyo Kasei Chemical, Tokyo Japan) aqueous solution and mixed thoroughly. This mixture is remained stationarily for one hour at a room temperature of 25 degrees or higher, or for 80 minutes at a temperature range between 20 and 25 degrees. During one hour, or 80 minutes, the leucocytes and part of the erythrocytes are concentrating in the surface region of the mixture, and this concentrated substance is collected and subjected to a centrifugal precipitation step at 1000 rpm. Thus produced clear supernatant is thrown away. RLB (hypotonic solution, produced by Harajuku Clinic, Tokyo Japan) is firstly added to the remaining solution, and after 30 seconds, BELMAR (hypertonic solution, produced by Harajuku Clinic, Tokyo Japan) is added to it. By this process, white, cheese-like layer is formed. If this white layer is not successfully formed by this first attempt, then the addition of the hypotonic solution and the hypertonic solution may be repeated until the white layer is formed. This white layer is subjected again to the centrifugal precipitation at 1000 rpm and its clear supernatant is removed. The precipitate is added with RPMI-1640 (tissue culture medium, produced by GIBCO BRL, USA) and 5% FBS (fetal bovine serum), and they are remained in an incubator under the condition of 5% carbon dioxide, at 37 degrees for 48 hours.

Figure 1A:
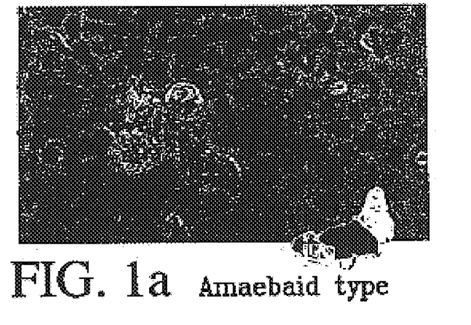
FIGS. 1a, 1b, 1c, 1d, 1e, 1f, and 1g illustrate photographic data captured through a phase-contrast microscope showing exemplar classifications of leucocytes cultured for 48 hours.
Figure 1B:
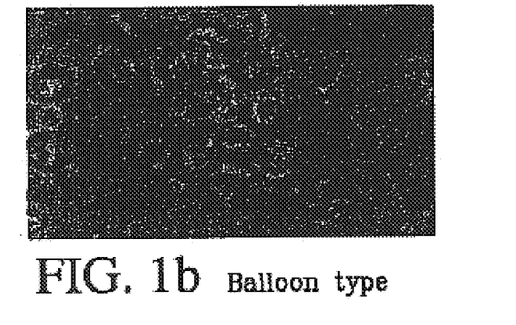
Figure 1C:
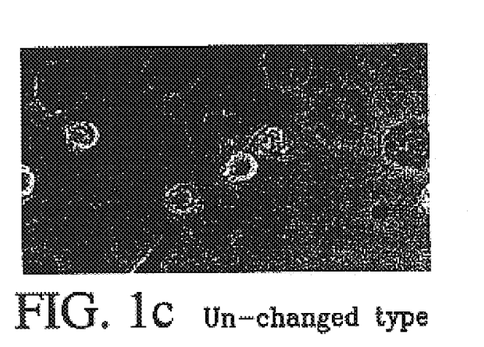
Figure 1D:
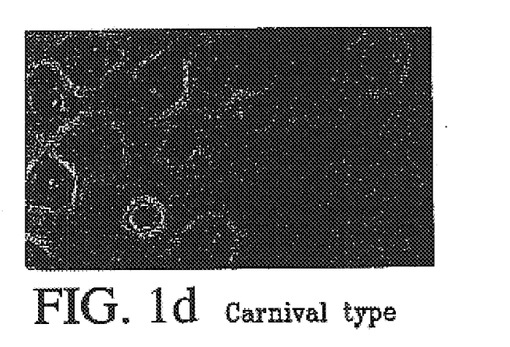
Figure 1E:
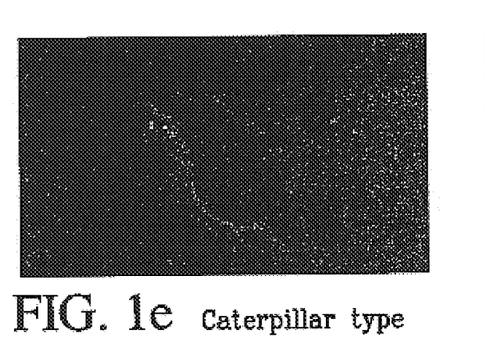
Figure 1F:
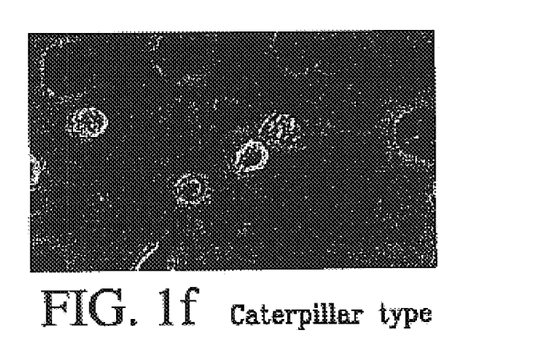
Figure 1G:
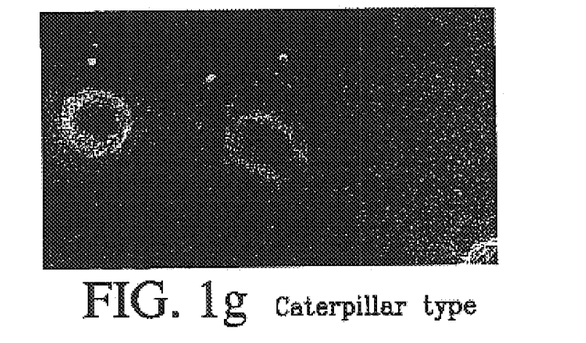

After 48 hours, the incubated sample is observed through a phase-contrast microscope (Nikon TMS-FMFA2010).The leucocytes after 48 hours incubation change into the following five shapes as shown in FIG. 1.

FIG. 1 shows five type photographs representing (1) carnival type cells (++++~v), (2) cells with no change (++~+++), (3) balloon type cells (++~+++), (4) caterpillar type cells (++~+++), and (5) amoeba type cells (+), in order of counted numbers. These name of five types are given by the present inventor according to their appearances.

The leucocyte solution after 48 hours incubation is further subjected to a centrifugal precipitation at 1000 rpm, and its clear supernatant is removed. This remained precipitate is washed by 20 to 50 ml of Physiosol No. 3 and centrifuged. These washing and centrifugal precipitation steps are repeated twice. Thus obtained leucocyte precipitate is additionally added with 100 to 200 ml of Physiosol No. 3, and maintained at 5 degrees or lower. This is designated Sample A. In the actually performed therapy for rheumatoid arthritis, the inventor infuses this Sample A intravenously within 24 hours.

Second, in order to clarify the therapeutic effects owing to the cultured leucocytes (Sample A), one typical test is performed as follows. Three fractionated blood samples provided by the method for fractionating erythrocytes are respectively inoculated with bacteria and their changes are observed. In detail, 10 ml of blood sample (including all blood ingredients) is taken from a healthy person. This blood sample is mixed with 15 ml of 7% Dextran aqueous solution and stirred sufficiently. Then this mixture is remained stationarily for 60 to 75 minutes at a room temperature from 20 to 25 degrees. This mixture is separated into three layers; i.e., top layer, middle layer, and bottom layer. Respective blood samples are separately taken from these three layers by means of a pipette. Four to six drops of each blood sample are added into a flask (produced by Costar) including 3 ml of a liquid culture medium RPMI-1640. Thus prepared blood samples are designated Sample B (containing types T, M, and B). Additionally, these cultured samples in the flasks are inoculated with bacteria such as pseudomonas sp. and remained in an incubator under the condition of 5% carbon dioxide, at 37 degrees.

Figure 2A:
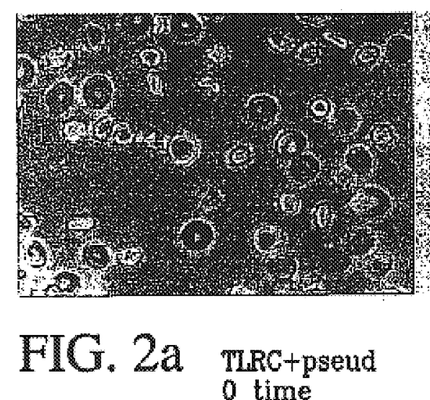
FIGS. 2a, 2b, 2c, 2d, 2e, and 2f illustrate photographic data captured through a phase-contrast microscope showing fractionated blood samples prepared by a method for fractionating red blood cells of human blood including one series photographed immediately after inoculation with bacteria, and another series photographed 24 hours later.
Figure 2B:
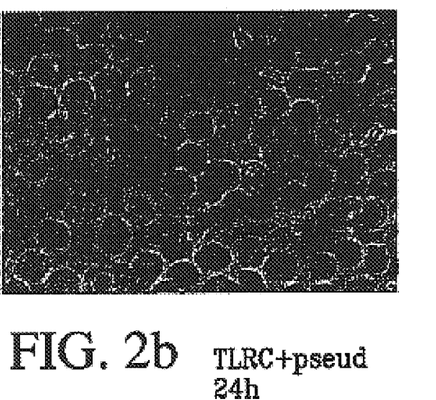
Figure 2C:
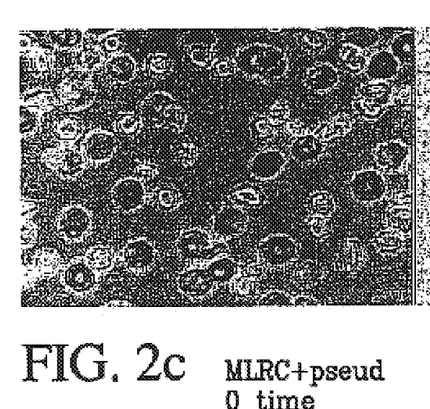
Figure 2D:
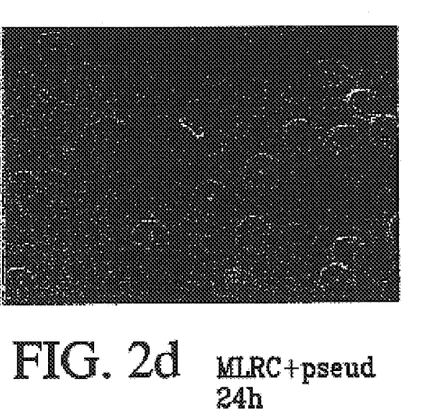
Figure 2E:
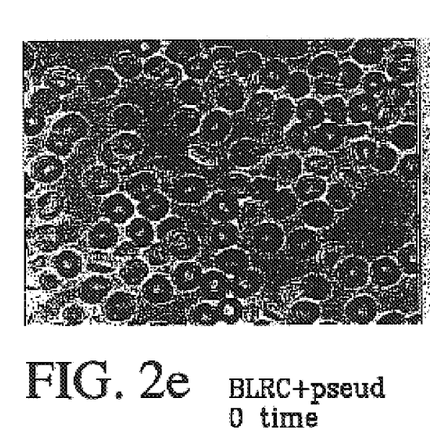
Figure 2F:
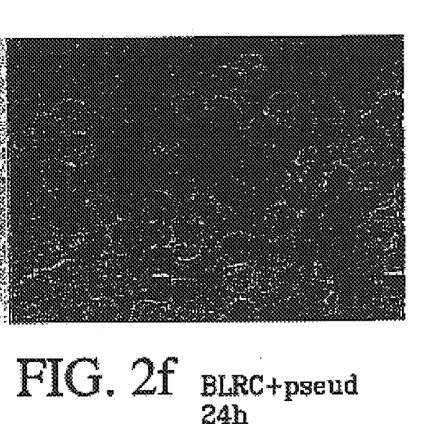

The changes of the Samples B, (types T, M and B) are observed through the phase-contrast microscope at immediately after the bacteria incubation, and after 24 hours. Thus resulted photographic data are shown in FIG. 2. The photograph No. 1 denotes the top layer of the fractionated red blood cells immediately after the bacteria incubation. The photograph No. 2 denotes the top layer after 24 hours. The photograph No. 3 denotes the middle layer immediately after the bacteria incubation. The photograph No. 4 denotes the middle layer after 24 hours. The photograph No. 5 denotes the bottom layer immediately after the bacteria incubation. The photograph No. 6 denotes the bottom layer after 24 hours. These photographic data indicate that the bacterial proliferation in the top and middle layers are inhibited to a certain extent owing to the leucocytes included in these layers inherently, while the bacterial proliferation in the bottom layer is not inhibited.

Figure 3A:
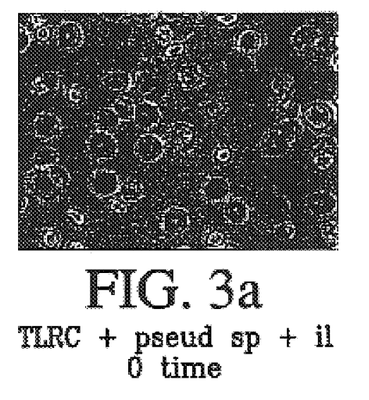
FIGS. 3a, 3b, 3c, 3d, 3e, 3f, 3h, 3j, 3k, 3l illustrate photographic data captured through a phase-contrast microscope showing fractionated blood samples prepared by a method for fractionating red blood cells of human blood including one series photographed immediately after inoculation with bacteria and incubated leucocytes or antibiotics, and another series photographed, alternately, 39 hours later or 28 to 29 hours later.
Figure 3B:
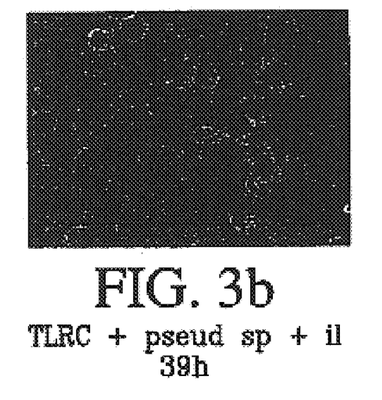
Figure 3C:
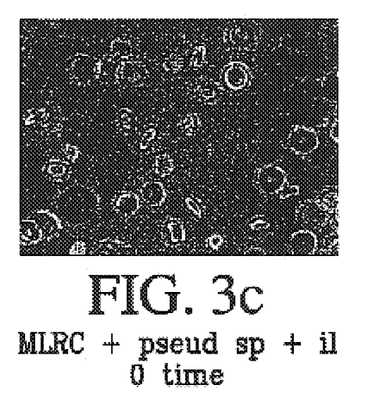
Figure 3D:
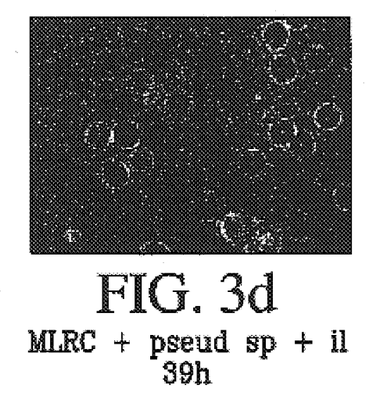
Figure 3E:
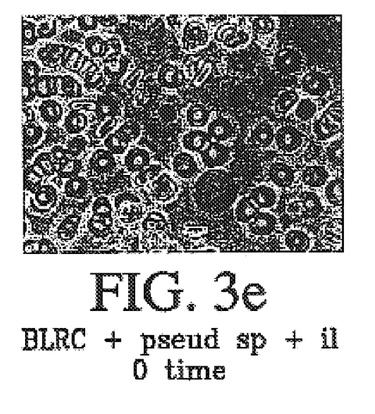
Figure 3F:
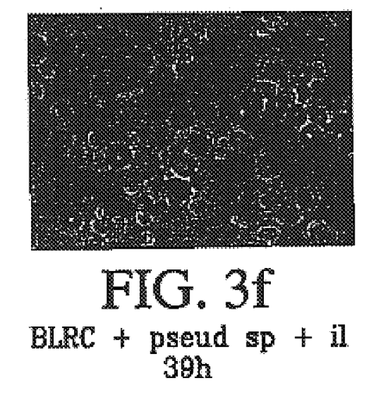
Figure 3G:
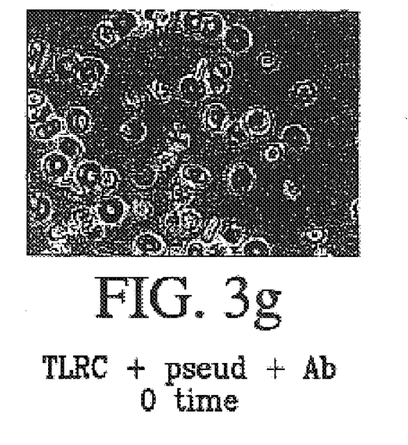
Figure 3H:
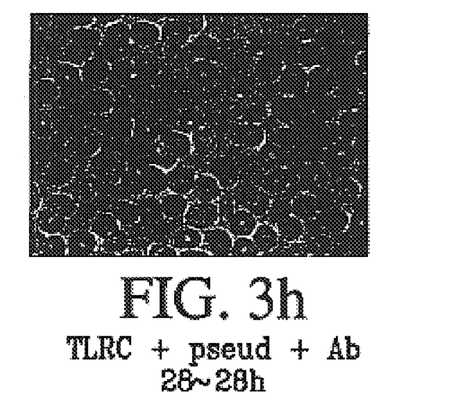
Figure 3I:
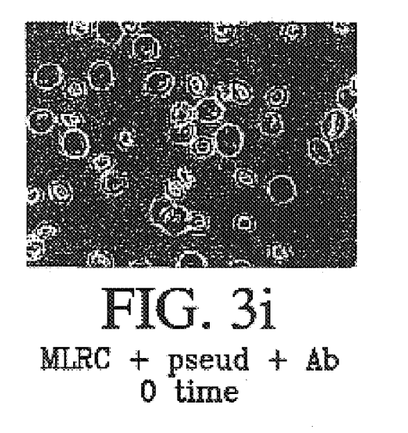
Figure 3J:
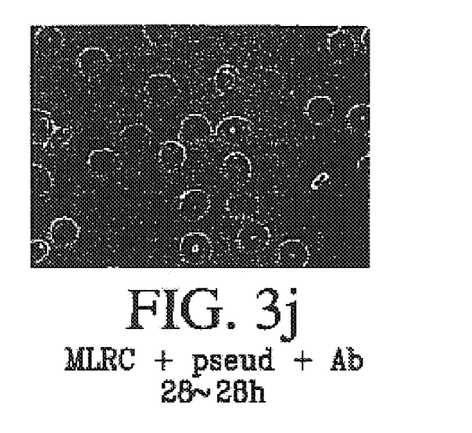
Figure 3K:
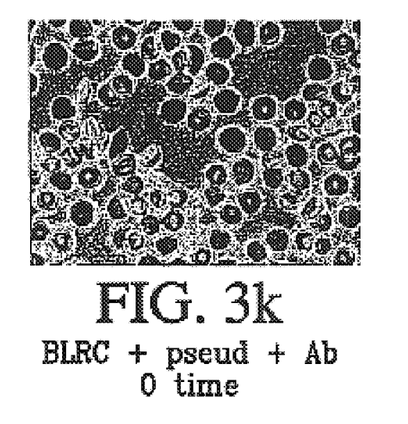
Figure 3L:
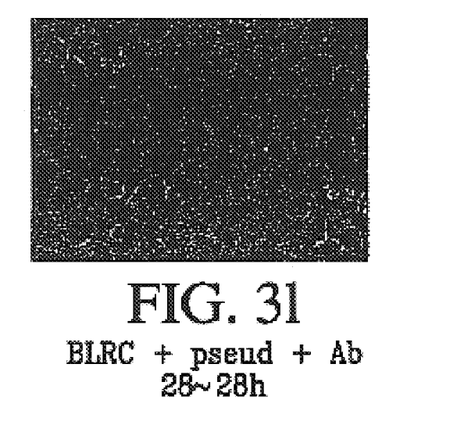

Next, the three fractionated blood samples (corresponding to Sample B) are inoculated with bacteria such as pseudomonas sp. and simultaneously mixed with the cultured leucocytes (corresponding to Sample A). The changes of the Samples B (types T, M and B) are observed through the phase-contrast microscope at immediately after the bacteria incubation and the leucocytes administration, and after 39 hours. Thus resulted photographic data are shown in FIG. 3. The photograph No. 1 denotes the top layer of the fractionated red blood cells immediately after the bacteria incubation and the leucocytes administration. The photograph No. 2 denotes the top layer after 39 hours. The photograph No. 3 denotes the middle layer immediately after. The photograph No. 4 denotes the middle layer after 39 hours. The photograph No. 5 denotes the bottom layer immediately after. The photograph No. 6 denotes the bottom layer after 39 hours. The photographs No. 7 to No. 12 correspond to No. 1 to No. 6 except for replacing the leucocytes administration with the antibiotics administration, respectively.

These photographic data No. 1 to No.6 indicate that the bacterial proliferation in the bottom layer subjected to the cultured leucocytes administration is slightly inhibited in addition to the top and middle layers. As shown in No. 7 to No. 10, although the bacterial proliferation in the top and middle layers is remarkably inhibited owing to the antibiotics, such inhibition effect is gradually degraded as time passes. No. 11 and No. 12, the bottom layer samples, do not show such inhibition effect at all even though the antibiotics are added to the bottom layer samples. This phenomenon cannot be explained by the conventional MIC (minimum inhibitory concentration) theory. Since this conventional theory is based on various experiments in vitro using glass vessels, the actual effects caused by antibiotics in vivo; i.e., human body, can not be correctly explained by this conventional theory.

The administration of cultured leucocytes allows the erythrocytes to enhance their inhibition effect for bacterial proliferation at least as same as antibiotics. Particularly, as time passes, the inhibition effect owing to the antibiotics is degraded rather than the cultured leucocytes. As is well known, the harmful aftereffects are caused by using antibiotics and some bacteria will acquire the resistance to the specific antibiotics which have been frequently used. The leucocytes are inherently existed in human body and known as a key-element for controlling spontaneous cure. Although the above described therapeutic test shows one example which uses one of bacteria to clarify the therapeutic effect caused by the cultured leucocytes, the same process of this test can also judge the therapeutic effects to various diseases such as various virus diseases, cancers, hepatic disease, renal disease and soon by using blood samples obtained from the patients suffering from these diseases. For example, in the case of patients suffering from type C hepatitis and dialysis, when the cultured leucocytes obtained from the patients themselves are added to their blood samples, their erythrocytes become poor in their activity and quality within 4 or 5 days. When the cultured leucocytes of a healthy person are added to these patients' blood samples, their erythrocytes maintain their initial activity and quality for a relatively long period. Additionally, the administration of the healthy person's cultured leucocytes to these patients' blood samples enhances the inhibition effect for bacterial proliferation remarkably. The similar effects are shown in the case of patients suffering from cancer and rheumatism.

As shown in FIG. 1, the 48 hours cultured leucocytes are classified into five shape groups in accordance with the microscopic observation. The cultured leucocytes used for the currrently performed therapy include all components of the five groups. If the component of the leucocytes having the therapeutic effects is specified, then this specified component will be chemically synthesized or extracted so as to realize superior drugs free from harmful aftereffects caused by currently used antibiotics. In other words, the object of the present invention is to provide a method for separating a single component from the leucocytes prior to the research on the relation between the leucocyte component and the therapeutic effect.

In the method for separating and collecting the leucocyte components from the above described cultured leucocytes according to one preferred embodiment of the present invention, the leucocyte cells are fractured as follows. The cultured leucocyte sample is frozen at the temperature range from −5 degrees to −72 degrees, preferably −20 degrees, and remained under such freezing condition for 10 days. This frozen leucocyte sample is defrosted at a room temperature within 1 to 3 hours. The defrosted leucocyte sample is subjected to a centrifugal precipitation from a low speed of 5 to 50 rpm to a high speed of 800 rpm. This centrifugal precipitation forms separated layers. Alternatively, the defrosted leucocyte sample is subjected to an electrophoresis process. This process also forms separated parts. Thus separated layers or parts are individually collected.

The physical means for fracturing the cell membranes of leucocytes is not limited to the above described freezing and defrosting process, but can be also selected from a supersonic method for applying the supersonic of 1 MHz to 50 MHz to the blood liquid containing leucocytes to fracture the cell membranes of leucocytes by the vibration caused by the supersonic; a laser method for irradiating the laser of 10 to 100 mW, 50/cm$^2$ for several seconds to several minutes (about 3 minutes) to the same point in the blood liquid containing leucocytes to fracture the cell membranes; an osmotic pressure method for changing the osmotic pressure of the blood liquid containing leucocytes to fracture the cell membranes; and a vacuum method for rapid-reducing the pressure in a vacuum chamber to fracture the cell membranes of the blood liquid containing leucocytes set in the chamber.

The collected component belonging to each of the separated layers or parts is subjected to the above described therapeutic tests to clarify its therapeutic effects for various bacteria and diseases and the functions for treating stale or perished cells. The therapeutic effects means that the spontaneous curing ability caused by the correlation between leucocytes and erythrocytes to inhibit the proliferation of bacteria or virus is returned to the normal person's level. The diseases disclosed above means various cancers, hepatitis, nephritis, rheumatoid arthritis, various inflammatory diseases, infectious diseases of virus or rickettsias, AIDS, or the like. In order to find which leucocyte component enhances the activity of erythrocytes remarkably, each one of the components separated and collected by the method according to the present invention is added to the blood samples obtained from the patients suffering from these diseases. Since it is possible to generate multiplier effects, two or three components may be combined to improve therapeutic effects.

As is clear from the above description, the method provided by the present invention can fracture the leucocyte-cell membrane to separate and collect the leucocyte components. If the component of the leucocytes having the therapeutic effects is specified, then this specified component will be chemically synthesized or extracted so as to realize superior drugs free from harmful aftereffects caused by currently used antibiotics. Particularly, in C type hepatitis, autoimmune hepatitis, and renal diseases, the correlation between leucocytes and erythrocytes is not normally performed and the activity of erythrocytes is degraded. This causes that the leucocytes' function for treating stale or perished cells becomes poor and these stale or perished cells are accumulated in hepatic and renal tissues. This accumulation results in the diseases of kidney and liver. If the function of the leucocyte components for treating stale or perished cells is clarified, a new drug which is free from harmful aftereffects produced by antibiotics and steroid drugs will be produced.

In another study in which the applicant explored the process by which in vivo cells are replaced with new cells through metabolism and the manner in which old cells are discharged from the body through kidneys and liver, the following experiment was performed:

Materials and Method 5 ml of blood collected from cubital veins was put into 7.5 ml of Matsumoto reagent (physiological saline with 7% of dextran), thoroughly mixed and stored at room temperature (below 20 degrees for about 1 hour. The blood then separated into three layers (upper, intermediate and lower layers). After individually collecting the three layers of blood (named groups U, I and L), each group was put into 3 ml of RPNI-1640 solution and was cultured at 37 degrees in a C02 incubator.

Frozen leucocytes or living leucocytes were added to group L without leucocytes (Both leucocytes and group L should be the same blood type).

The patient's leucocytes and frozen healthy person's leucocytes were adding into ULRBC and LILRBC each, and there were incubated.

Results

Group U (upper layer) changed into fine particles although the particle sizes varied greatly between different diseases.

Group I (intermediate layer) also changed into fine particles.

Group L (lower layer) contains some unusual cells, which the author named "dry shells" and "pockmarks". These cells were observed among fine particles.

"Dry shells" and "pockmarks" disappeared after incubation. No particle was found in the carcass of the leucocytes and two kinds of matter, which applicant named "fire fly" and "ghost". This seems to indicate that, unlike the case without the addition of leucocytes, cellular components were easily subdivided and became water-soluble.

Figure 4A:
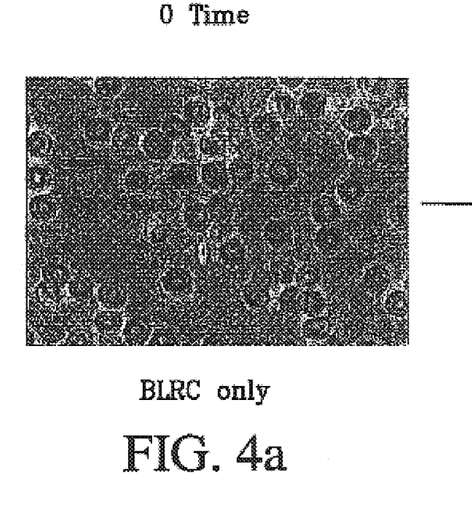
FIGS. 4a, 4b, 4c, and 4d illustrate photographic data captured through a phase-contrast microscope illustrating a comparison of BLCR incubated both, with and without leucocytes over a period of 9 days.
Figure 4B:
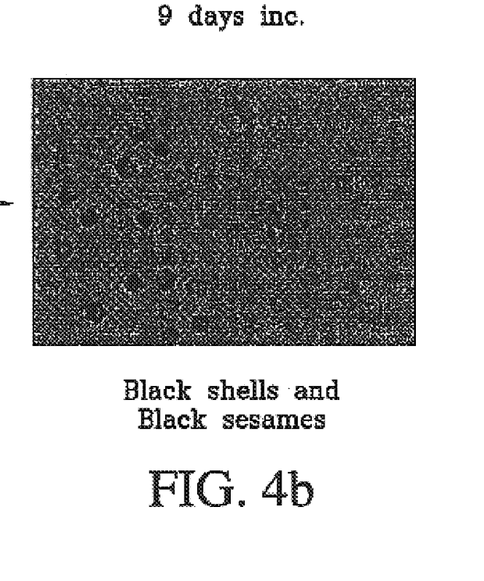
Figure 4C:
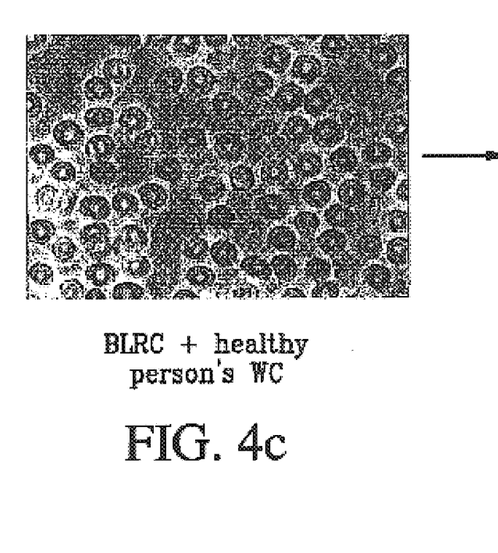
Figure 4D:
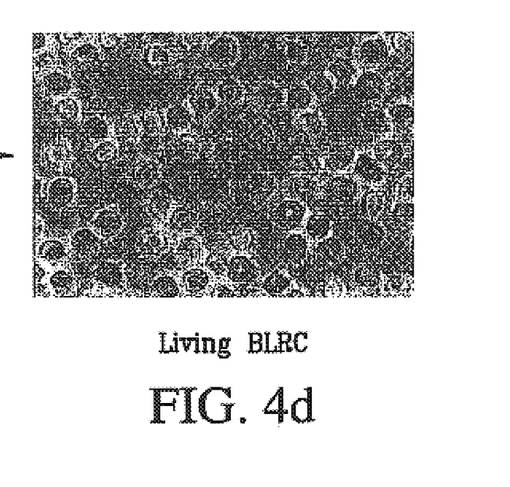

Although the question of how dead erythrocytes are subdivided and become water-soluble and are excreted from the body as well as the question of how the cells of organs with high metabolisms (i.e., muscle, liver and heart) are actively excreted are still unsolved, this study has proven that the last particles of LLRBC, which are supposed to remain in the forms of "black shells" or "pockmark", can be decomposed and become water-soluble as a result of adding leucocytes (see FIG. 4).

The fact that frozen leucocytes worked more active than living leucocytes suggests that components of leucocytes might have acted on the particles. This indicates that short-lived leucocytes are working to decompose and subdivide erythrocytes as well as to change erythrocytes into water-soluble.

Furthermore, it is assumed that, without such functions of leucocytes, "black shells" or "pockmarks" deposit on the tissues of kidneys or liver, and in the end, trigger the dysfunction of these organs. Further examination is necessary on this point.

In a still further study, the interaction between White Blood Cells (Wbcs) and Red Blood Cells (Rbc) was examined using the M-H method.

The M-H Method 5 to 10 ml of peripheral blood and Matsumoto reagent (7% dextran saline solution) in a ratio of 1 to 1.5, were mixed and left at room temperature for 40 to 60 minutes. The erythrocytes of the 3 layers, the top, middle and bottom, were separated, extracted alive, and incubated.

Results

1. The ULRbc (upper layer red cells) which contains Wbcs have the action of suppressing the proliferation of bacteria. However, the LLRbc (lower layer red cell) which do not contain Wbcs do not have this action. The phagocytosis by Wbc was not observed in either of the layer cells.

2. The life span of the RCs existing in one drop of blood containing WC, in the ULRbc, and in the ILRbc were longer compared to that of the Rbcs in the LLRbc, which do not contain Wbcs. In healthy persons, the life span of the Rbcs were prolonged when Wbcs were added.

3. When Wbcs from another person with identical blood types were added to the blood cells containing the Fish-type red blood cells, the Fish-type cells disappeared and turned into normal red blood cell The Wbcs had an effect on certain types of red blood cells.

4. The WCs die in 7 to 10 days when alone, but the life span of the Wbcs was prolonged remarkably, and they grew huge in the ULRbc and ILRbc of certain diseases, such as cancer, rheumatism, herpes, and drug rash. That is, the Rbcs of the ULRbc and ILRbc caused the white cells to grow huge and prolonged their life span.

5. When Wbcs were added to the LLRbc, the life span of the LLRbc was prolonged.

Figure 5A:
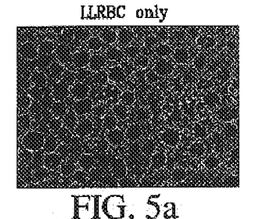
Figure 5B:
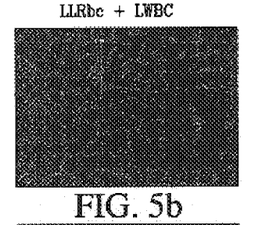
Figure 5C:
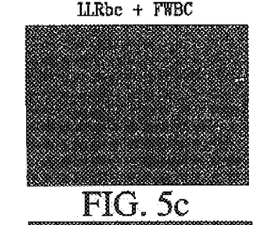
Figure 5D:
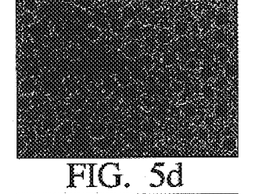
Figure 5E:
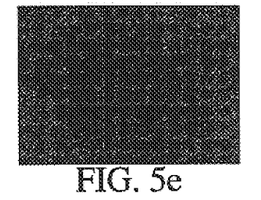
Figure 5F:
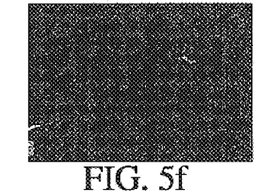
Figure 5G:
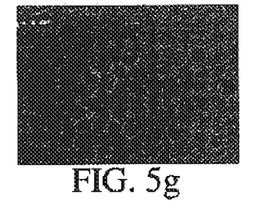
Figure 5H:
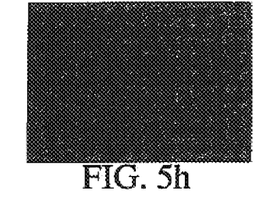

6. When LWbc (living white blood cells) and FWbc (frozen white blood cells) were added to the LLRbc and incubated, the components of the LLRbc turned into small water-soluble substances at the time of death and became invisible. In other words, the Wbcs or the components of the Wbcs were involved in the dissolution and absorption of the LLRbc, which accounts for more than 97% of the red blood cells. (see FIG. 5)

Figure 6A:
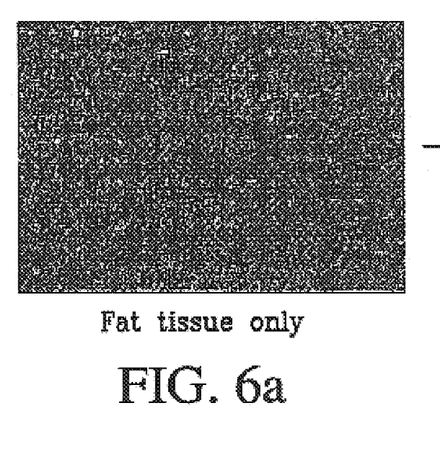
FIGS. 6a, 6b, 6c, and 6d illustrate photographic data captured through a phase-contrast microscope illustrating the effects of adding and incubating white blood cells with muscle and fat tissue.
Figure 6B:
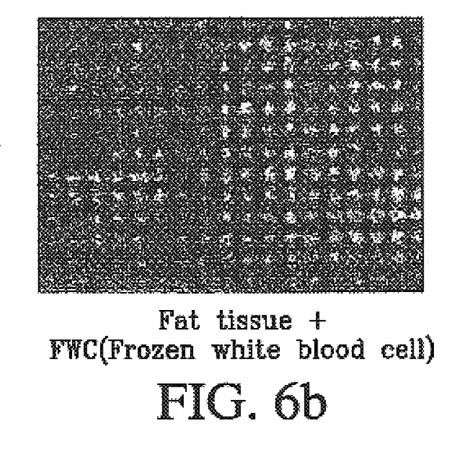
Figure 6C:
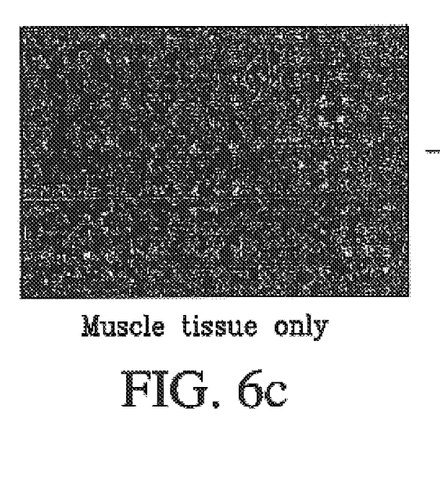
Figure 6D:
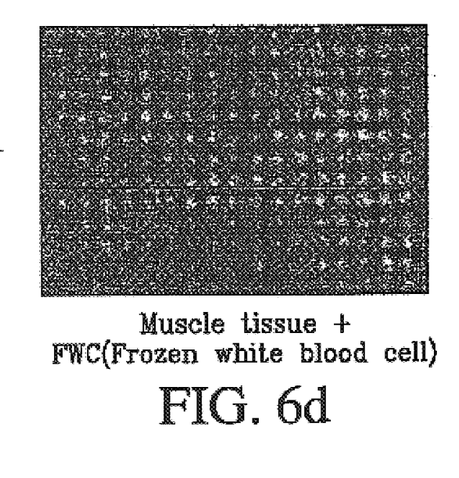

7. When LWbc and FWbc were added to the muscle tissue or Fat tissue and incubated, Muscle cells and Fat cells turned into small water-soluble substances at the time of death and became invisible. (see FIG. 6)

8. When the ULRbc, which contains Wbcs, was incubated using Costar's Transwell, the red blood cell of the ULRbc increased. (It did not always increase in the LLRbc and ILRbc.)

9. When the white blood cells from the synovial fluid were placed into ULRbc, many of them turned into the caterpillar type, and when placed into the LLRbc, many of them turned into the balloon type. The Wbc placed in the ILRbc showed change that was in between the changes seen in the ULRbc and in the LLRbc. The unchanged type of Wbcs always existed to a certain degree in both layers. This shows that the Rbc had an effect on the change in the Wbcs.

10. As with the Wbcs in full blood, when the leucocytes in the synoval fluid from a rheumatism case were placed in the ULRbc, ILRbc and LLRbc, a strong suppressing action against the proliferation of the bacteria was observed in the ULRbc. However, the action was weak in the LLRbc. The Wbcs showed no action of phagocytosis in any of the layers.

11. In the case of certain diseases, such as cancer, rheumatism, and hepatitis, when a drop of blood was incubated, a large number of Wbcs quickly turned into deformed cells called the β-type leucocytes, then dissolved, and disappeared.

Figure 7A:
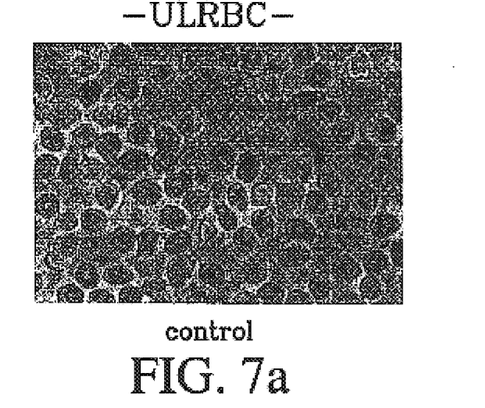
FIGS. 7a, 7b, 7c, 7d, 7e, and 7f illustrate photographic data captured through a phase-contrast microscope illustrating the effects of adding WBCS from both a healthy person and a diabetic patient into upper and lower layer RBCs.
Figure 7B:
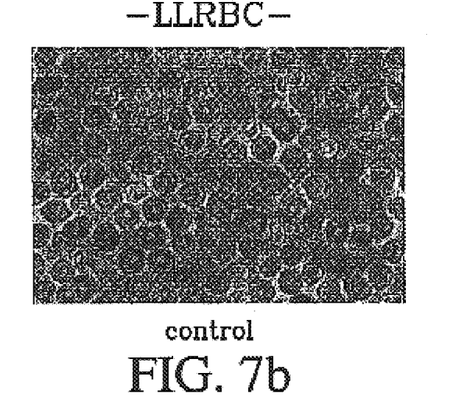
Figure 7C:
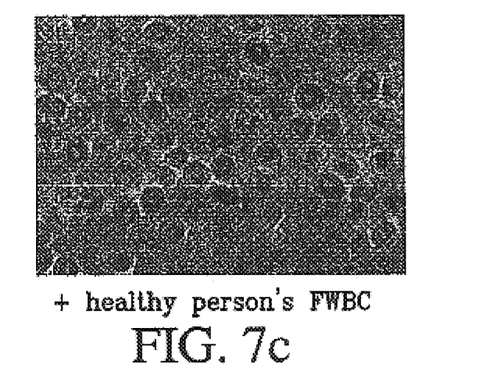
Figure 7D:
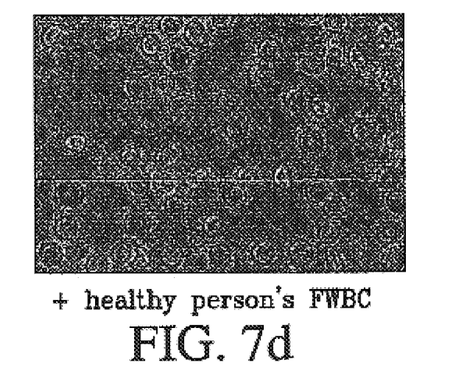
Figure 7E:
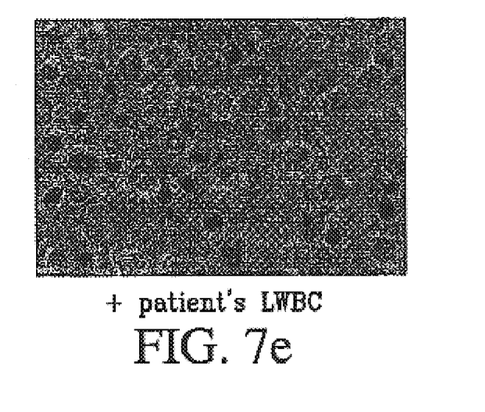
Figure 7F:
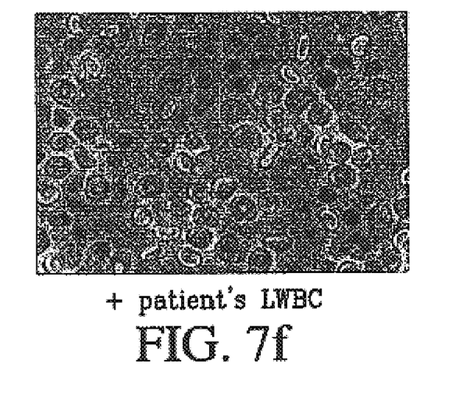

12. When Wbcs from a patient under dialysis due to kidney failure were placed into her own ULRbc and LLRbc, the Rbcs started changing rapidly from the 4th day, and the grapes (Blue-grapes) type, Deformed RCs and the black spots increased. On the other hand, when Wbcs from healthy persons were placed in the layer cells, the Rbcs did not change. It has become clear that the Wbcs of the patient under dialysis had bad effect on his own Rbcs. (see FIG. 7)

Figure 8A:
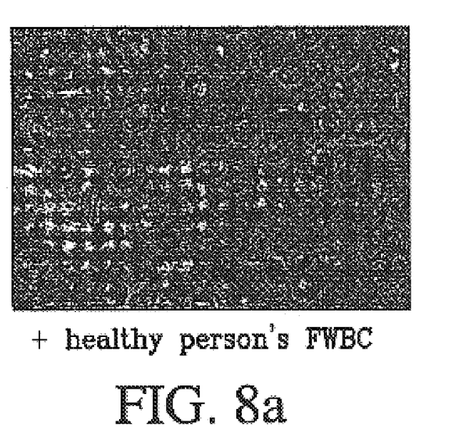
FIGS. 8a, 8b, 8c, and 8d illustrate photographic data captured through a phase-contrast microscope illustrating the results of adding frozen and living white blood cells from both a healthy parson and a patient with hepatitis to ULRBCs.
Figure 8B:
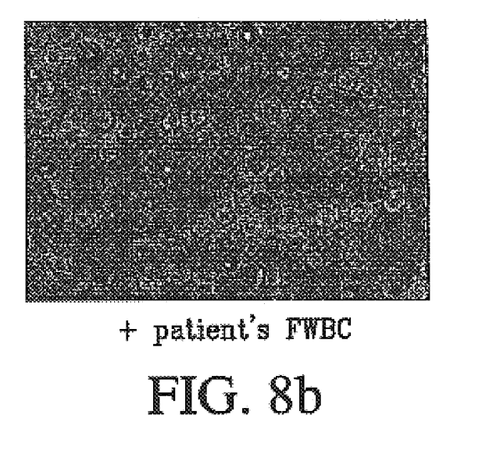
Figure 8C:
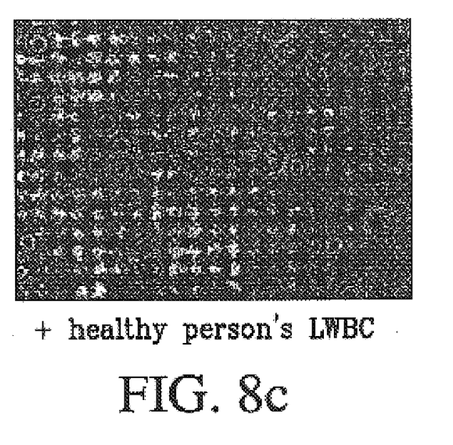
Figure 8D:
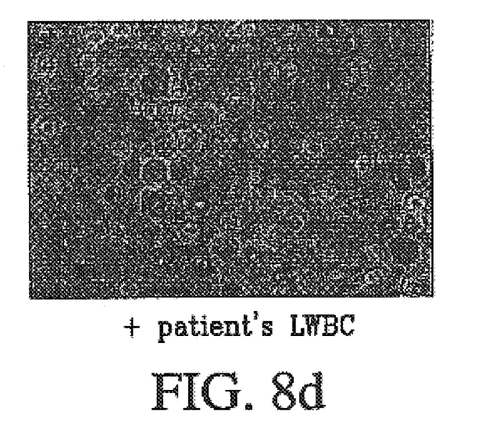
Figure 9A:
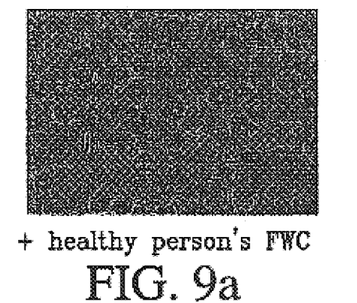
FIGS. 9a, 9b, 9c, 9d, 9e, 9f, 9g, and 9h illustrate photographic data captured through a phase-contrast microscope illustrating a comparison of the results of incubating frozen and living white blood cells from both a healthy person and a hepatitis patient with both TLRC and BLRC.
Figure 9B:
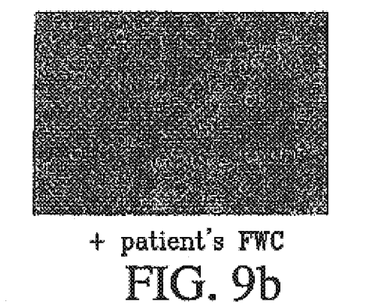
Figure 9C:
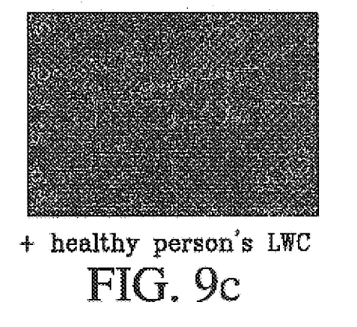
Figure 9D:
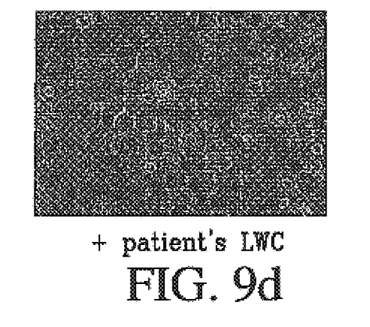
Figure 9E:
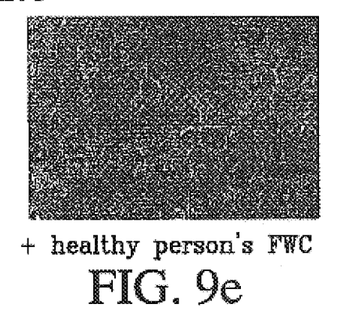
Figure 9F:
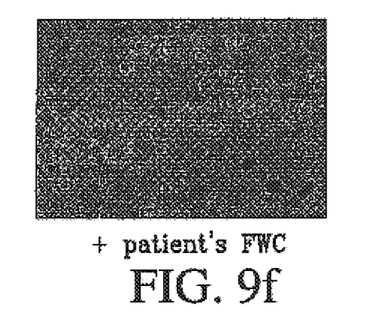
Figure 9G:
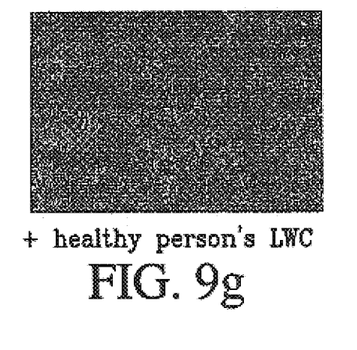
Figure 9H:
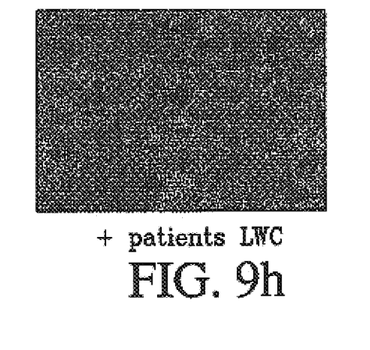
Figure 10:
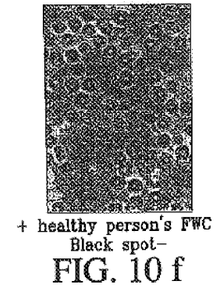
FIGS. 10a, 10b, 10c, 10d, 10e, 10f, 10g, and 10h illustrate photographic data captured through a phase contrast microscope illustrating a comparison of the effects on erythrocyte activity of the addition of living and frozen white blood cells from both a healthy person and a hepatitis patient.
Figure 10A:
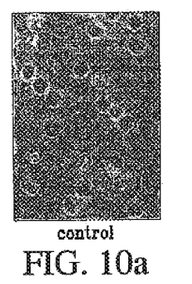
Figure 10B:
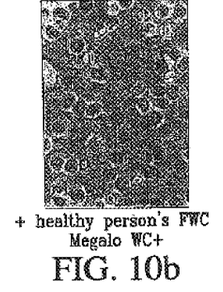
Figure 10C:
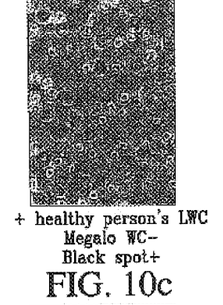
Figure 10D:
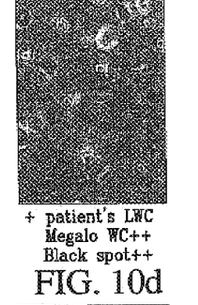
Figure 10E:
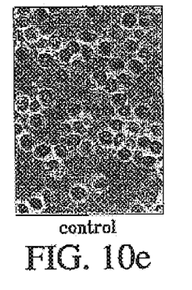
Figure 10G:
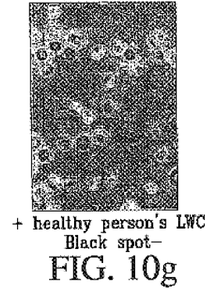
Figure 10H:
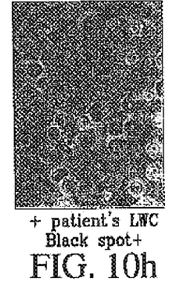

13. When LWbcs from a patient with autoimmune hepatitis and with C hepatitis were added to his own ULRbc and LLRbc, orange cells and Blue-grapes increased as well as the black spots. However, when LWbcs or FWbcs from a healthy person were added, black spots as well as the orange cells were remarkably small in number. It is clear that the patient's Wbcs had bad effect on his own Rbcs. (see FIGS. 8–10)

As many apparently widely different embodiments of this invention may be made without departing from the spirit and scope thereof, it is to be understood that the invention is not limited to the specific embodiments thereof except as defined in the appended claims.

What is claimed is:

1. A method for obtaining leucocyte components from human blood comprising;
    (A) a first step for fracturing cell membranes of leucocytes of human blood by physical means, and
    (B) a second step for separating leucocyte components from blood liquid resulting from the first step, said blood liquid containing leucocytes with fractured cell membranes, in order so that separated layers or parts can be collected individually; and further comprising a step for determining therapeutic effects of separated and collected leucocyte components, said step including combining isolated leucocyte components with blood cells obtained from a patient with a pro-determined disease and thereafter observing effects of said isolated leucocyte components when combined with said blood cells.

2. A method of identifying a therapeutically effective leucocyte component comprising:
    fracturing cell membranes of leucocytes cultured from healthy human blood by physical means and isolating leucocyte components obtained therefrom;
    obtaining blood cells from a patient with a pre-determined disease and separating said blood cells into upper layer blood cells and lower layer blood cells;
    dividing each of said upper layer blood cells and lower layer blood cells into a plurality of test samples;
    adding said isolated leucocyte components to said plurality of test samples thereby to determine the therapeutic effect of each said isolated leucocyte component on said blood cells; and
    selecting a leucocyte component therapeutically effective for treating said pre-determined disease by identifying the component which, when added to said test samples, results in the least degeneration of erythrocytes and longest erythrocyte life span.

3. The method according to claim 2 wherein the physical means for fracturing cell membranes is a method selected from the group consisting of:
    (a) a supersonic method for applying supersonic sound waves selected from between 1 MHz and 50 MHz to said healthy human blood containing leucocytes in order to fracture said cell membranes of leucocytes by vibration thereof;
    (b) a laser method employing a laser having a selected from between 10 and 100 mW for irradiating said healthy human blood for a time up to about 3 minutes in order to fracture said cell membranes of said leucocytes;
    (c) an osmotic pressure method for changing an osmotic pressure of said healthy human blood containing leucocytes to fracture said cell membranes;
    (d) a freezing and defrosting method for freezing said healthy human blood containing leucocytes at a temperature selected from between −5 degrees Celsius to absolute zero and thereafter defrosting said frozen blood at about room temperature to fracture said cell membranes; and
    (e) a vacuum method for rapidly-reducing pressure in a vacuum chamber to fracture said cell membranes of said healthy human blood containing leucocytes in said vacuum chamber.

4. The method according to claim 2 wherein prior to said cell membrane fracturing step, said leucocytes obtained from healthy human blood are incubated.

5. The method according to claim 4 wherein said leucocytes obtained from healthy human blood are incubated for approximately 48 hours.

6. The method according to claim 4 wherein said upper and lower layer blood cells are incubated prior to adding said isolated leucocyte components.

7. The method according to claim 6 wherein said upper and lower layer blood cells are mixed with tissue culture medium and thereafter incubated at approximately 37 degrees Celsius in approximately 5% carbon dioxide.

8. The method according to claim 6 further including an additional step wherein after said isolated leucocyte components are added to said test samples, said test samples, in combination with said isolated leucocyte components, are incubated.

* * * * *